United States Patent [19]

Haga et al.

[11] Patent Number: 4,740,619
[45] Date of Patent: Apr. 26, 1988

[54] PHENYLHYDRAZONOCYCLOHEXANONE OXIMES

[75] Inventors: Toru Haga, Ibaraki; Eiki Nagano, Nishinomiya; Masayuki Takase, Takarazuka; Ryo Sato, Toyonaka, all of Japan

[73] Assignee: Sumitomo Chemical Company, Limited, Osaka, Japan

[21] Appl. No.: 13,405

[22] Filed: Feb. 3, 1987

Related U.S. Application Data

[62] Division of Ser. No. 656,745, Oct. 1, 1984, Pat. No. 4,668,278.

[30] Foreign Application Priority Data

Nov. 9, 1983 [JP] Japan ................................. 58-211331
Dec. 5, 1983 [JP] Japan ................................. 58-229631

[51] Int. Cl.$^4$ ........................................ C07C 131/04
[52] U.S. Cl. .................................... 564/249; 564/253
[58] Field of Search ................. 548/257, 259, 260; 564/249, 253

[56] References Cited

U.S. PATENT DOCUMENTS

| | | | |
|---|---|---|---|
| 3,197,475 | 7/1965 | Carboni | 548/257 |
| 3,897,421 | 7/1975 | Aebli | 548/255 |
| 3,978,074 | 8/1976 | Jancis | 548/259 |
| 4,240,822 | 12/1980 | Diehl et al. | 548/259 |

FOREIGN PATENT DOCUMENTS

| | | | |
|---|---|---|---|
| 1572237 | 6/1969 | France | 548/257 |
| 48-1140 | 1/1973 | Japan | 71/92 |
| 932154 | 7/1963 | United Kingdom | 548/259 |

OTHER PUBLICATIONS

Butula, Chem. Abstracts, vol. 75, No. 36052f (1971), p. 516.
Buechel et al, Chem. Abstracts, vol. 78, No. 16190h (1973).

*Primary Examiner*—Donald G. Daus
*Assistant Examiner*—Mark W. Noel
*Attorney, Agent, or Firm*—Birch, Stewart, Kolasch & Birch

[57] ABSTRACT

A compound of the formula:

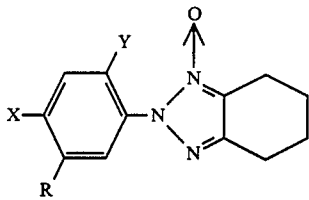

wherein R is a hydrogen atom, a $C_1$–$C_4$ alkoxy group, a $C_1$–$C_4$ alkenyloxy group, a $C_3$–$C_4$ alkynyloxy group, a $C_1$–$C_4$ alkylthio group, a dichlorocyclopropylmethoxy group or a methyldichlorocyclopropylmethoxy group, X is a chlorine atom or a bromine atom and Y is a hydrogen atom, a fluorine atom or a chlorine atom, which is useful as a herbicide.

1 Claim, No Drawings

PHENYLHYDRAZONOCYCLOHEXANONE OXIMES

This application is a divisional of copending application Ser. No. 656,745, filed on Oct. 1, 1984, now U.S. Pat. No. 4,668,278.

The present invention relates to 4,5,6,7-tetrahydro-1,2,3-benzotriazol-1-oxides (hereinafter referred to as "benzotriazoles"), and their production and use.

Said benzotriazoles are representable by the formula:

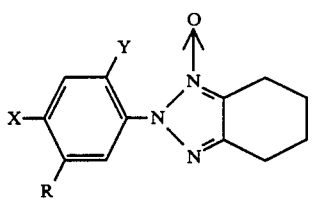

wherein R is a hydrogen atom, a $C_1$–$C_4$ alkoxy group, a $C_3$–$C_4$ alkenyloxy group, a $C_3$–$C_4$ alkynyloxy group, a $C_1$–$C_4$ alkylthio group, a dichlorocyclopropylmethoxy group or a methyldichlorocyclopropylmethoxy group, X is a chlorine atom or a bromine atom and Y is a hydrogen atom, a fluorine atom or a chlorine atom.

It has now been found that the benzotriazoles (I) show a strong herbicidal activity against a wide variety of weeds including broad-leaved weeds, Graminaceous weeds, Commelinaceous weeds and Cyperaceous weeds in agricultural plowed fields by foliar or soil treatment and do not produce any material phytotoxicity on various agricultural crops (i.e. corn, wheat, rice plant, soybean, cotton, sugarbeet). Examples of broad-leaved weeds which can be controlled or exterminated by the benzotriazoles (I) are wild buckwheat (*Polygonum convolvulus*), pale smartweed (*Polygonum lapathifolium*), common purslane (*Portulaca oleracea*), common lambsquarters (*Chenopodium album*), redroot pigweed (*Amaranthus retroflexus*), garden radish (*Raphanus sativus*), wild mustard (*Sinapis arvensis*), shepherdspurse (*Capsella bursa-pastoris*), hemp sesbania (*Sesbania exaltata*), sicklepod (*Cassia tora*), velvetleaf (*Abutilon theophrasti*), prickly sida (*Sida spinosa*), field pansy (*Viola arvensis*), ivyleaf morningglory (*Ipomoea hederifolia*), tall morningglory (*Ipomoea purpurea*), field bindweed (*Convolvulus arvensis*), red deadnettle (*Lamium purpureum*), henbit (*Lamium amplexicaure*), jimsonweed (*Datura stramonium*), black nightshade (*Solanum nigrum*), birdseye speedwell (*Veronica persica*), ivyleaf speedwell (*Veronica hederaefolia*), heartleaf cocklebur (*Xanthium strumarium*), common sunflower (*Helianthus annuus*), scentless chamomile (*Matricaria inodola*), corn marigold (*Chrysnathemum segetum*), etc. Examples of Graminaceous weeds against which the benzotriazoles (I) show a herbicidal activity are Japanese millet (*Echinochloa frumentacea*), common barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), common oat (*Avena sativa*), wild oat (*Avena fatua*), Johnsongrass (*Sorghum halepense*), downy brome (*Bromus tectorum*), etc. Examples of Commelinaceous weeds are asiatic dayflower (*Commelina communis*), etc. Examples of Cyperaceous weeds are rice flatsedge (*Cyperus iria*), etc. It has also been found that the benzotriazoles (I) can control or exterminate in paddy fields broad-leaved weeds such as common falsepimpernel (*Lindernia procumbens*), toothcup (*Rotala indica*), waterwort (*Elatine triandra*), Graminaceous weeds such as barnyardgrass (*Echinochloa oryzicola*), Cyperaceous weeds such as smallflower sedge (*Cyperus difformis*), hardstem bulrush (*Scirpus juncoides*), slender spikerush (*Eleocharis acicularis*), nutsedge (*Cyperus serotinus*) and paddy-field weeds such as pickerelweed (*Monochoria vaginalis*), arrowhead (*Sagittaria pygmaea*), waterplantain (*Alisma canaliculatum*), while exerting no material phytotoxicity to rice plants. Accordingly, the benzotriazoles (I) can be used as herbicides applicable to agricultural plowed fields as well as paddy fields without exerting any material chemical injury to soybean and rice plants.

Among the benzotriazoles (I) of the present invention, those wherein R is a $C_1$–$C_4$ alkoxy group, a $C_3$–$C_4$ alkenyloxy group or a $C_3$–$C_4$ alkynyloxy group, X is a chlorine atom or a bromine atom and Y is a hydrogen atom or a fluorine atom are preferred. Particularly preferred are 2-(4-chloro-2-fluoro-5-methoxyphenyl)-4,5,6,7-tetrahydro-1,2,3-benzotriazol-1-oxide, 2-(4-chloro-2-fluoro-5-propargyloxyphenyl)-4,5,6,7-tetrahydro-1,2,3-benzotriazol-1-oxide, 2-(4-chloro-2-fluoro-5-allyloxyphenyl)-4,5,6,7-tetrahydro-1,2,3-benzotriazol-1-oxide, etc.

The benzotriazoles (I) of the present invention may be prepared by the following procedures:

Procedure (a)

The benzotriazole of the formula:

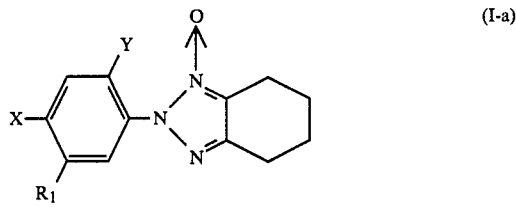

wherein $R_1$ is a hydrogen atom, a $C_1$–$C_4$ alkoxy group or a $C_1$–$C_4$ alkylthio group and X and Y are each as defined above is obtainable by subjecting a 2-phenylhydrazonocyclohexanone oxime of the formula:

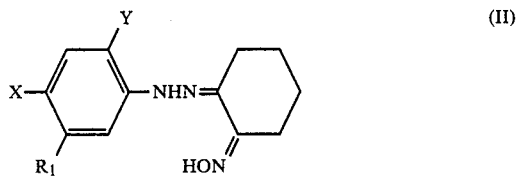

wherein $R_1$, X and Y are each as defined above to ring closure, i.e. reacting with an oxidizing agent in a solvent at a temperature of 0° to 100° C. for a period of 0.5 to 10 hours.

As the solvent, there may be used aliphatic hydrocarbons (e.g. hexane, heptane), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. dioxane, tetrahydrofuran, diethylene glycol dimethyl ether), alcohols (e.g. ethanol, isopropanol, t-butanol, octanol, cyclohexanol, methyl cellosolve, diethylene glycol, glycerol), esters (e.g. ethyl formate, ethyl acetate, butyl acetate, diethyl carbonate), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), ammonia water, water, etc. They may be employed alone or in combination.

Examples of the oxidizing agent are mercury oxide, lead tetraacetate, cupric salts (e.g. cupric sulfate). The use of an aqueous solution of cupric sulfate in the presence of pyridine is particularly preferred. The amount of the oxidizing agent may be usually from 1 to 1.5 equivalents to the 2-phenylhydrazinocyclohexanone oxime (II).

After completion of the reaction, the reaction mixture may be subjected to post-treatment such as extraction with an organic solvent or concentration to obtain the objective compound (I-a). If necessary, purification by chromatography or recrystallization may be adopted.

Procedure (b)

The benzotriazole of the formula:

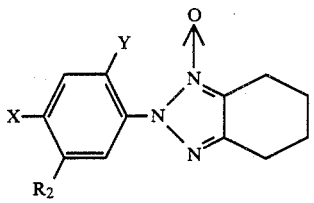
(I-b)

wherein $R_2$ is a $C_1$–$C_4$ alkoxy group, a $C_3$–$C_4$ alkenyloxy group, a $C_3$–$C_4$ alkynyloxy group, a dichlorocyclopropylmethoxy group or a methyldichlorocyclopropylmethoxy group and X and Y are each as defined above is obtainable by reacting a 2-hydroxyphenyl-4,5,6,7-tetrahydro-1,2,3-benzotriazol-1-oxide of the formula:

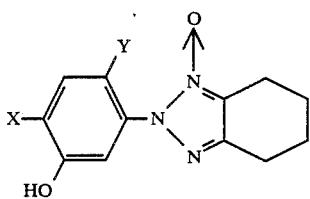
(III)

wherein X and Y are each as defined above with a compound of the formula:

$R_2$—Z    (IV)

wherein Z is a halogen atom, an alkyl-substituted phenylsulfonate group or an alkylsulfonate group and $R_2$ is as defined above in a solvent in the presence of a dehydrohalogenating agent at a temperature of 0° to 150° C. for a period of 0.5 to 24 hours. If necessary, a phase transfer catalyst may be present in the reaction system.

The amounts of the compound (IV), the dehydrohalogenating agent and the phase transfer catalyst may be respectively from 1.0 to 1.5 equivalents, from 1.0 to 1.5 equivalents and from 0.01 to 0.1 equivalent to the compound (III).

As the solvent, there may be exemplified aromatic hydrocarbons (e.g. benzene, toluene, xylene), ketones (e.g. acetone, methyl ethyl ketone), amides (dimethylformamide, dimethylacetamide), sulfoxides (e.g. dimethylsulfoxide), ethers (e.g. tetrahydrofuran, diethyl ether, ethylene glycol dimethyl ether), nitriles (e.g. acetonitrile), water, etc. These may be used solely or in combination.

Examples of the dehydrohalogenating agent are inorganic bases (e.g. sodium carbonate, potassium carbonate, sodium hydroxide, potassium hydroxide), organic bases (e.g. pyridine, triethylamine, N,N-dimethylaniline, N,N-diethylaniline), etc.

As the phase transfer catalyst, there may be used tetrabutylammonium bromide, tributylbenzylammonium chloride, triethylbenzylammonium bromide, etc. Further, potassium iodide or a monovalent copper salt is occassionally added as a reaction accelerator.

After completion of the reaction, the reaction mixture may be subjected to post-treatment such as extraction with an organic solvent or concentration to obtain the objective compound (I-b). If necessary, purification by chromatography or recrystallization may be adopted.

Practical and presently preferred embodiments for production of the benzotriazoles (I) are illustratively shown in the followng Examples.

EXAMPLE 1

(Procedure (a))

To a solution of 2-(4-chlorophenylhydrazono)-cyclohexanone oxime (1.6 g) in a mixture of 15% aqueous solution of pyridine (25 ml) and tetrahydrofuran (20 ml), a solution of cupric sulfate (CuSO$_4$.5H$_2$O) (2.5 g) in water (10 ml) was added at room temperature, and the resultant mixture was heated under reflux for 2 hours. After cooling, water was added to the mixture, which was then extracted with ethyl acetate. The extract was washed with a saturated aqueous cupric sulfate solution and water in order, dried and concentrated. The residue was purified by silica gel column chromatography using a mixture of n-hexane and ethyl acetate as an eluent to give 0.2 g of 2-(4-chlorophenyl)-4,5,6,7-tetrahydro-1,2,3-benzotriazol-1-oxide (Compound No. 1). M.P., 100°–101° C.

EXAMPLE 2

(Procedure (b))

To a mixture of 2-(4-chloro-2-fluoro-5-hydroxyphenyl)-4,5,6,7-tetrahydro-1,2,3-benzotriazol-1-oxide (1 g), potassium carbonate (0.3 g) and dimethylformamide (5 ml), propargyl bromide (0.6 g) was added, and the resultant mixture was stirred at 70° to 80° C. for 4 hours. After cooling, water was added to the mixture, which was then extracted with ethyl acetate. The organic layer was washed with water, dried and concentrated. The residue was purified by silica gel thin layer chromatography using a mixture of n-hexane and ethyl acetate as a developing solvent to give 0.15 g of 2-(4-chloro-2-fluoro-5-propargyloxyphenyl)-4,5,6,7-tetrahydro-1,2,3-benzotriazol-1-oxide (Compound No. 12). M.P., 155°–156° C.

In the same manner as above, there are produced the benzotriazoles (I), of which some typical examples are shown in Table 1.

TABLE 1

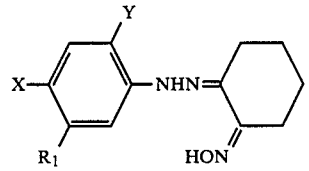

(I)

| Compound No. | X | Y | R | Physical constant |
|---|---|---|---|---|
| 1 | Cl | H | H | M.P. 100–101° C. |
| 2 | Cl | F | H | M.P. 146–146.5° C. |
| 3 | Cl | H | iso-$C_3H_7O$ | M.P. 108–109° C. |
| 4 | Cl | H | $C_2H_5O$ | Glassy |
| 5 | Cl | F | $CH_3O$ | M.P. 120–122° C. |
| 6 | Cl | F | n-$C_3H_7O$ | M.P. 61–61.5° C. |
| 7 | Cl | F | iso-$C_3H_7O$ | M.P. 109–109.8° C. |
| 8 | Cl | Cl | iso-$C_4H_9O$ | M.P. 100–101° C. |
| 9 | Cl | F | iso-$C_3H_7S$ | M.P. 89–91° C. |
| 10 | Br | H | H | M.P. 102–103° C. |
| 11 | Cl | H | $HC\equiv CCH_2O$ | M.P. 136–137° C. |
| 12 | Cl | F | $HC\equiv CCH_2O$ | M.P. 155–156° C. |
| 13 | Cl | F | $HC\equiv C-CH(CH_3)$— | $n_D^{24}$ 1.5668 |
| 14 | Cl | F | $H_2C=CHCH_2O$ | $n_D^{24}$ 1.5732 |
| 15 | Cl | F | 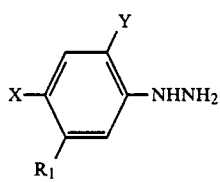 | M.P. 73–74° C. |
| 16 | Cl | F | 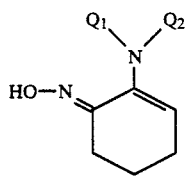 | Glassy |

The 2-phenylhydrazonocyclohexanone oxime (II), i.e. the starting material for production of the compound (I-a), may be prepared by reacting a phenylhydrazine compound of the formula:

wherein $R_1$, X and Y are each as defined above with a 1.0 to 1.1 equivalent amount of a cyclohexene compound of the formula:

wherein $Q_1$ and $Q_2$ are, the same or different, each a lower alkyl group or, when taken together with the nitrogen atom to which they are attached, they may form a ring containing or not an oxygen atom in a solvent in the presence of a catalytic amount of an acid at a temperature of 0° to 100° C. for a period of 0.5 to 12 hours.

As the acid, there may be used acetic acid, dilute hydrochloric acid or the like. Examples of the solvent are methanol, ethanol, ethylene glycol monomethyl ether, ethylene glycol, etc.

Upon completion of the reaction, the reaction mixture is subjected to post-treatment such as extraction with an organic solvent or concentration to obtain the 2-phenylhydrazonocyclohexanone oxime (III). If necessary, the purification by chromatography or recrystallization may be adopted.

A typical example for production of the 2-phenylhydrazonocyclohexanone oxime (II) is as follows:

EXAMPLE 3 p-Chlorophenylhydrazine (1.42 g) was added to a mixture of N-(2-hydroxyimino-1-cyclohexenyl)morpholine (1.96 g) and ethanol (15 ml) containing a catalytic amount of acetic acid, and the resultant mixture was heated under reflux for 3 hours. After cooling, ethanol was removed from the mixture by distillation under reduced pressure, and water was added thereto, followed by extraction with ethyl acetate. The organic layer was washed with water, dried and concentrated. The residue was purified by silica gel column chromatography using a mixture of n-hexane and ethyl acetate as an eluent to give 1.6 g of 2-(4-chlorophenylhydrazono)cyclohexanone oxime as a red glassy material.

In the same manner as above, there were produced the 2-phenylhydrazonocyclohexanone oximes (II), of which typical examples are shown in Table 2.

TABLE 2

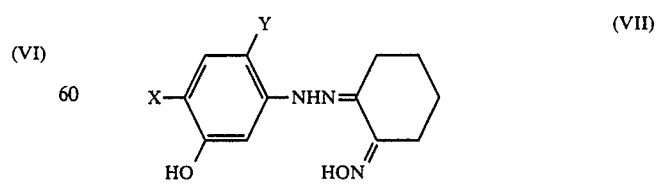

| Compound No. | X | Y | $R_1$ | Physical constant |
|---|---|---|---|---|
| a | Cl | F | $CH_3O$ | M.P. 190–191° C. |
| b | Cl | F | iso-$C_3H_7O$ | M.P. 156–156.5° C. |
| c | Cl | F | H | M.P. 187–189° C. (decomp.) |

The 2-hydroxyphenyl-4,5,6,7-tetrahydro-1,2,3-benzotriazole-1-oxide (III) as the starting material in production of the benzotriazoles (I-b) is obtainable by reacting a hydrazone compound of the formula:

wherein X and Y are each as defined above with a 1.0 to 1.5 equivalent amount of an oxidizing agent in a solvent at a temperature of 0° to 150° C. for a period of 1.0 to 24 hours.

The solvent usable in the reaction are water, tetrahydrofuran, pyridine, ether, etc. These may be used solely or in combination.

Examples of the oxidizing agent are lead tetra-acetate, mercury oxide, cupric salts, etc. Among them, the use of a cupric salt in the presence of a base such as pyridine is favorable.

Upon completion of the reaction, the reaction mixture is subjected to post-treatment such as extraction with an organic solvent or concentration to obtain the 2-hydroxyphenyl-4,5,6,7-tetrahydro-1,2,3-benzotriazol-1-oxide (III). If necessary, purification by chromatography or recrystallization may be adopted.

The hydrazone compound (VII) can be obtained by diazotization of an aniline compound of the formula:

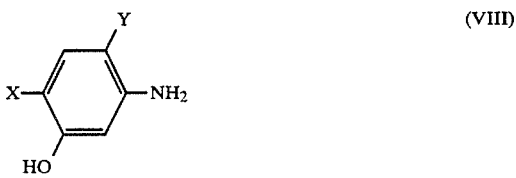

(VIII)

wherein X and Y are each as defined above at a temperature of $-10°$ to $10°$ C. and reducing the diazotized aniline compound at a temperature of $-30°$ to $-10°$ C. with a reducing agent such as stannous chloride to give a phenylhydrazine compound of the formula:

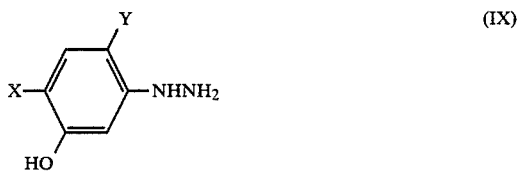

(IX)

wherein X and Y are each as defined above. This phenylhydrazine compound (IX) is then reacted with a 1.0 to 1.1 equivalent amount of the cyclohexene compound (VI) in a solvent at a temperature of $0°$ to $100°$ C. for a period of 0.5 to 12 hours to give the hydrazone compound (VII). If necessary, a catalytic amount of an acid may be present in the reaction.

As the acid, there may be used acetic acid, dilute hydrochloric acid or the like. Examples of the solvent are methanol, ethanol, ethylene glycol monomethyl ether, ethylene glycol, etc.

Upon completion of the reaction, the reaction mixture is subjected to post-treatment such as extraction with organic solvent or concentration. When desired, the reaction product may be purified by chromatography or recrystallization to give the hydrazone compound (VII).

Some typical examples for production of the 2-hydroxyphenyl-4,5,6,7-tetrahydro-1,2,3-benzotriazol-1-oxide (III) are set forth below:

EXAMPLE 4

4-Chloro-2-fluoro-5-hydroxyaniline (32.5 g) was added to conc. hydrochloric acid (300 ml), and a solution of sodium nitrite (15.2 g) in water (20 ml) was added thereto at $0°$ to $-5°$ C. The resultant mixture was stirred at 0 to $5°$ C. for 30 minutes, and urea was added thereto to remove excessive nitrite ion, followed by cooling to $-30°$ C. A solution of stannous chloride (92 g) in hydrochloric acid (160 ml) was added thereto, and the mixture was stirred at $0°$ to $-10°$ C. for 3 hours. The reaction mixture was filtered, and the precipitated crystals were dissolved in water, neutralized with sodium hydroxide and extracted with ethyl acetate. The organic layer was washed with water, dried and concentrated. The residue was treated with ether to give 4-chloro-2-fluoro-5-hydroxyphenylhydrazine (8.4 g) as crystals. The crystals were added to a solution of 2-hydroxyiminocyclohexanone morpholinoenamine (9.35 g), ethanol (90 ml) and a catalytic amount of acetic acid and heated under reflux for 3 hours. After cooling, ethanol was removed by evaporation, and water was added to the residue, followed by extraction with ethyl acetate. The extract was dried and concentrated, and the residue was purified by silica gel chromatography using a mixture of ethyl acetate and n-hexane as an eluent to give 2-(4-chloro-2-fluoro-5-hydroxyphenyl)-hydrazonocyclohexanone oxime (8 g) as crystals. The crystals were suspended in a mixture of tetrahydrofuran (50 ml) and 15% pyridine-water (112 ml). A solution of cupric sulfate (CuSO$_4$.5H$_2$O) (11.2 g) in water (40 ml) was added to the suspension, which was heated under reflux for an additional 2 hours. After cooling, water was added to the mixture, which was then extracted with ethyl acetate. The organic layer was washed with an aqueous solution of cupric sulfate, dried and concentrated. The residue was purified by silica gel chromatography using a mixture of ethyl acetate and n-hexane as an eluent to give 2-(4-chloro-2-fluoro-5-hydroxyphenyl)-4,5,6,7-tetrahydro-1,2,3-benzotriazol-1-oxide (4 g) as crystals. M.P., 220°–221° C. (decomp.).

EXAMPLE 5

In the same manner as in Example 4 but using 4-chloro-3-hydroxyaniline, there was produced 2-(4-chloro-3-hydroxyphenyl)-4,5,6,7-tetrahydro-1,2,3-benzotriazol-1oxide. M.P., 189°–191° C. (decomp.).

On the practical usage of the benzotriazole (I) as a herbicide, it may be applied in any preparation form such as emulsifiable concentrate, wettable powder, suspension, granules, etc. in combination with a conventional solid or liquid carrier or diluent, a surface active agent and/or an auxiliary agent.

The content of the benzotriazole (I) as the active ingredient in said preparation form may be usually within a range of 0.01 to 90% by weight, preferably of 0.05 to 80% by weight.

Examples of the solid carrier or diluent are fine powders or granules of kaolin clay, attapulgite clay, bentonite, terra alba, pyrophyllite, talc, diatomaceous earth, calcite, walnut powders, urea, ammonium sulfate, synthetic hydrated silicon dioxide, etc. As the liquid carrier or diluent, there may be exemplified aromatic hydrocarbons (e.g. xylene, methylnaphthalene), alcohols (e.g. isopropanol, ethylene glycol, celosolve), ketones (e.g. acetone, cyclohexanone, isophorone), plant oils (e.g. soybean oil, cotton seed oil), dimethylsulfoxide, acetonitrile, water, etc. The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agents include ligninsulfonates, alginates, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts and % are by weight. The compound number of the active ingredient corresponds to the one in Table 1.

FORMULATION EXAMPLE 1

Fifty parts of Compound No. 5 or 12, 3 parts of calcium ligninsulfonate, 2 parts of sodium laurylsulfate and 45 parts of synthetic hydrated silicon dioxide are well mixed to obtain a wettable powder.

FORMULATION EXAMPLE 2

Ten parts of Compound No. 1 or 13, 14 parts of polyoxyethylenestyrylphenyl ether, 6 parts of calcium dodecylbenzenesulfonate and 70 parts of cyclohexanone are well mixed to obtain an emulsifiable concentrate.

FORMULATION EXAMPLE 3

Two parts of Compound No. 6 or 14, 1 part of synthetic hydrated silicon dioxide, 2 parts of calcium ligninsulfonate, 30 parts of bentonite and 65 parts of kaolin clay are well mixed. The mixture is then kneaded with water, granulated and dried to obtain granules.

FORMULATION EXAMPLE 4

Twenty-five parts of Compound No. 9 or 12 is mixed with 3 parts of polyoxyethylene sorbitan monooleate, 3 parts of CMC (carboxymethyl cellulose) and 69 parts of water, and the mixture is pulverized until the particle size of the mixture becomes less than 5 microns to obtain a suspension.

The benzotriazoles (I) thus formulated in any suitable formulation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the benzotriazoles (I) over the top of plants. It may also be applied directly to weeds with care so as to keep the chemical off the crop foliage.

The benzotriazoles (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Besides, the benzotriazoles (I) can be used as herbicides applicable to agricultural plowed field as well as paddy field. They are also useful as herbicides to be employed for orchard, pasture land, forest, non-agricultural field, etc.

The dosage rate of the benzotriazoles (I) may vary on prevailing weather conditions, preparation used, prevailing season, mode of application, soil involved, crop and weed species, etc. Generally, however, the dosage rate may be from 0.05 to 80 grams, preferably from 0.1 to 40 grams, of the active ingredient per are. The herbicidal composition of the present invention prepared in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as stated above, polyoxyethylene resin acid (ester), ligninsulfonate, abietylenic acid salt, dinaphthylmethanedisulfonate, paraffin, etc. The composition prepared in the form of granules may be normally applied as such without dilution.

The biological effect of the benzotriazoles (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates that no material difference is seen in comparison with the untreated plant and the numeral "5" indicates the complete inhibition or death of the test plants.

The compounds shown in Table 3 below were used for comparison.

TABLE 3

| Compound No. | Chemical structure | Remarks |
| --- | --- | --- |
| A | 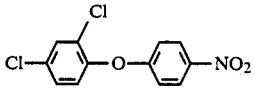 | Commercially available herbicide; "nitrofen" |
| B | 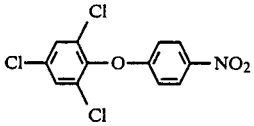 | Commercially available herbicide; "chlornitrofen" |
| C | 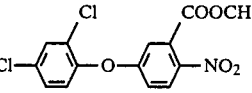 | Commercially available herbicide; "bifenox" |
| D | 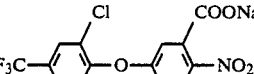 | Commercially available herbicide; "acifluorfen" |

TEST EXAMPLE 1

Cylindrical plastic pots (diameter, 10 cm; height, 10 cm) were filled with upland field soil, and the seeds of Japanese millet, common oat, tall morningglory and velvetleaf were sowed therein and covered with soil. A designed amount of the test compound formulated into a wettable powder according to Formulation Example 1 was diluted with water, and the dilution was sprayed onto the soil surface by means of a small hand sprayer at a spray volume of 10 liters per are. Thereafter, the test plants were grown in a greenhouse for 20 days, and the herbicidal activity was examined. The results are shown in Table 4.

TABLE 4

| | | Herbicidal activity | | | |
| --- | --- | --- | --- | --- | --- |
| Compound No. | Dosage (g/are) | Japanese millet | Common oat | Tall morning-glory | Velvet-leaf |
| 1 | 40 | 5 | 5 | 3 | 5 |
|   | 10 | 4 | 2 | 1 | 5 |
| 2 | 40 | 5 | 5 | 5 | 5 |
|   | 10 | 5 | 5 | 5 | 5 |
| 3 | 40 | 5 | 5 | 5 | 5 |
|   | 10 | 5 | 5 | 5 | 5 |
| 4 | 40 | 5 | 5 | 5 | 5 |

TABLE 4-continued

| Compound No. | Dosage (g/are) | Japanese millet | Common oat | Tall morning-glory | Velvet-leaf |
|---|---|---|---|---|---|
| | | Herbicidal activity | | | |
| 5 | 10 | 5 | 5 | 5 | 5 |
| 5 | 40 | 5 | 5 | 5 | 5 |
| | 10 | 5 | 5 | 5 | 5 |
| 6 | 40 | 5 | 5 | 5 | 5 |
| | 10 | 5 | 5 | 5 | 5 |
| 7 | 40 | 5 | 5 | 5 | 5 |
| | 10 | 5 | 5 | 5 | 5 |
| 8 | 40 | 5 | 5 | 5 | 5 |
| | 10 | 5 | 5 | 5 | 5 |
| 9 | 40 | 5 | 5 | 5 | 5 |
| | 10 | 5 | 5 | 5 | 5 |
| 10 | 40 | 5 | 5 | 3 | 5 |
| | 10 | 4 | 2 | 1 | 5 |
| 15 | 40 | 5 | 5 | 5 | 5 |
| 16 | 40 | 5 | 5 | 5 | 5 |
| | 10 | 5 | 5 | 4 | 5 |
| A | 40 | 5 | 5 | 3 | 5 |
| | 10 | 3 | 3 | 1 | 3 |
| B | 40 | 4 | 4 | 3 | 5 |
| | 10 | 2 | 2 | 1 | 3 |
| C | 40 | 4 | 4 | 4 | 5 |
| | 10 | 3 | 3 | 3 | 3 |

TEST EXAMPLE 2

Cylindrical plastic pots (diameter, 10 cm; height, 10 cm) were filled with upland field soil, and the seeds of Japanese millet, common oat, garden radish and velvetleaf were sowed therein and cultivated in a greenhouse for 10 days. A designed amount of the test compound formulated into an emulsifiable concentrate according to Formulation Example 2 was diluted with water containing a spreading agent, and the dilution was sprayed onto the foliage of the test plant by means of a small hand sprayer at a spray volume of 10 liters per are. Thereafter, the test plants were further grown in the greenhouse for 20 days, and the herbicidal activity was examined. The results are shown in Table 5.

TABLE 5

| Compound No. | Dosage (g/are) | Japanese millet | Common oat | Garden radish | Velvet-leaf |
|---|---|---|---|---|---|
| | | Herbicidal activity | | | |
| 1 | 20 | 5 | 3 | 5 | 5 |
| | 5 | 4 | 3 | 4 | 5 |
| 2 | 20 | 5 | 5 | 5 | 5 |
| | 5 | 5 | 5 | 5 | 5 |
| 3 | 20 | 5 | 5 | 5 | 5 |
| | 5 | 5 | 5 | 5 | 5 |
| 4 | 20 | 5 | 5 | 5 | 5 |
| | 5 | 5 | 5 | 5 | 5 |

TABLE 5 -continued

| Compound No. | Dosage (g/are) | Japanese millet | Common oat | Garden radish | Velvet-leaf |
|---|---|---|---|---|---|
| | | Herbicidal activity | | | |
| 5 | 20 | 5 | 5 | 5 | 5 |
| | 5 | 5 | 4 | 5 | 5 |
| 6 | 20 | 5 | 5 | 5 | 5 |
| | 5 | 5 | 5 | 5 | 5 |
| 7 | 20 | 5 | 5 | 5 | 5 |
| | 5 | 5 | 5 | 5 | 5 |
| 8 | 20 | 5 | 5 | 5 | 5 |
| | 5 | 5 | 5 | 5 | 5 |
| 9 | 20 | 5 | 5 | 5 | 5 |
| | 5 | 5 | 5 | 5 | 5 |
| 10 | 20 | 5 | 4 | 5 | 5 |
| | 5 | 4 | 3 | 4 | 5 |
| 15 | 20 | 5 | 4 | 5 | 5 |
| 16 | 20 | 5 | 5 | 5 | 5 |
| | 5 | 4 | 4 | 5 | 5 |
| A | 20 | 5 | 4 | 0 | 5 |
| | 5 | 3 | 2 | 0 | 3 |
| B | 20 | 5 | 2 | 3 | 5 |
| | 5 | 3 | 0 | 0 | 3 |
| C | 20 | 5 | 3 | 5 | 5 |
| | 5 | 2 | 3 | 5 | 5 |

TEST EXAMPLE 3

Vats (33 cm × 23 cm × 11 cm) were filled with upland field soil, and the seeds of tall morningglory, cocklebur, velvetleaf, sicklepod, johnsongrass and Japanese millet as well as the seeds of wheat, sugarbeet, corn, cotton and soybean were sowed therein at a depth of 1 to 2 cm. A designed amount of the test compound formulated into a wettable powder according to Formulation Example 1 was diluted with water, and the dilution was sprayed to the soil surface by means of a small hand sprayer at a spray volume of 10 liters per are. Thereafter, the test plants were grown in a greenhouse for 20 days, and the herbicidal activity was examined. The results are shown in Table 6.

TABLE 6

| Compound No. | Dosage (g/are) | Tall morning-glory | Cocklebur | Velvet-leaf | Sickle-pod | Johnson-grass | Japanese millet | Wheat | Sugar-beet | Corn | Cotton | Soy-bean |
|---|---|---|---|---|---|---|---|---|---|---|---|---|
| | | Herbicidal activity | | | | | | | | | | |
| 2 | 20 | 5 | 5 | 5 | 5 | 5 | 5 | 5 | 5 | 5 | 5 | 3 |
| | 5 | 0 | 5 | 5 | 4 | 5 | 5 | 4 | 5 | 4 | 3 | 2 |
| 6 | 10 | 5 | 5 | 5 | 4 | 5 | 5 | 5 | 5 | 4 | 1 | 1 |
| | 2.5 | — | 5 | 5 | — | 5 | 5 | 4 | 5 | 2 | 0 | 0 |
| 7 | 4 | 5 | 5 | 5 | 5 | — | 5 | — | — | 4 | — | — |
| | 1 | 5 | 1 | 5 | 4 | — | 5 | — | — | 3 | 1 | 0 |
| 8 | 20 | 3 | 2 | 5 | 0 | 5 | 5 | 4 | 5 | 1 | 0 | 1 |
| | 5 | 0 | 0 | 4 | 0 | 5 | 4 | 2 | 5 | 0 | 0 | 0 |
| 9 | 10 | 4 | 0 | 5 | 2 | 4 | 4 | 3 | 5 | 0 | 0 | 0 |
| | 2.5 | 2 | 0 | 5 | 0 | 2 | 2 | 0 | 4 | 0 | 0 | 0 |
| C | 40 | 4 | 4 | 5 | 3 | 2 | 4 | 4 | 5 | 1 | 5 | 0 |
| | 10 | 3 | 2 | 3 | 0 | 1 | 3 | 3 | 5 | 0 | 0 | 0 |

TEST EXAMPLE 4

Vats (33 cm × 23 cm × 11 cm) were filled with upland field soil, and the seeds of soybean, cotton, sugarbeet, corn and wheat as well as the seeds of tall morningglory, cocklebur, velvetleaf, sicklepod, Japanese millet, johnsongrass and green foxtail were sowed therein at a depth of 1 to 2 cm. A designed amount of the test compound formulated into an emulsifiable concentrate according to Formulation Example 2 was diluted with water, and the dilution was sprayed to the soil surface by means of a small hand sprayer at a spray volume of 10 liters per are. Thereafter, the test plants were grown in a greenhouse for 20 days, and the herbicidal activity was examimed. The results are shown in Table 7.

TEST EXAMPLE 8

TABLE 7

| Compound No. | Dosage (g/are) | Herbicidal activity | | | | | | | | | | |
|---|---|---|---|---|---|---|---|---|---|---|---|---|
| | | Soy-bean | Cotton | Sugar-beet | Corn | Wheat | Tall morning-glory | Cock-lebur | Velvet-leaf | Sickle-pod | Japanese millet | Johnson-grass | Green foxtail |
| 11 | 10 | 0 | 0 | 5 | 0 | 4 | 4 | 3 | 5 | 3 | 5 | 5 | 5 |
|  | 2.5 | 0 | 0 | 3 | 0 | 3 | 3 | 2 | 5 | — | 4 | 3 | 3 |
| 12 | 5 | 2 | 1 | 5 | 2 | 5 | 5 | 5 | 5 | — | 5 | 5 | 5 |
|  | 1.25 | 0 | 0 | 5 | 0 | 4 | 4 | 4 | 5 | — | 5 | 5 | 5 |
| 13 | 5 | 2 | 3 | 5 | 2 | 5 | 5 | 4 | 5 | 4 | 5 | 5 | 5 |
|  | 1.25 | 0 | 2 | 5 | 2 | 3 | 5 | — | 5 | — | 5 | 5 | 5 |
| 14 | 5 | 1 | 2 | 5 | 1 | 4 | 5 | 4 | 5 | 5 | 5 | 5 | 5 |
|  | 1.25 | 0 | 0 | 4 | 0 | 2 | 4 | — | 5 | 5 | 5 | 5 | 5 |
| 15 | 10 | 0 | — | — | — | — | 5 | 5 | 5 | — | 5 | 5 | 5 |
| 16 | 10 | — | 0 | — | 0 | — | 5 | 5 | 5 | — | — | 5 | 5 |
| D | 10 | 2 | 3 | 5 | 2 | 2 | 2 | 2 | 5 | 1 | 3 | 4 | 4 |
|  | 2.5 | 1 | 2 | 5 | 0 | 0 | 1 | 0 | 4 | 0 | 2 | 2 | 2 |

TEST EXAMPLE 5

Vats (33 cm × 23 cm × 11 cm) were filled with upland field soil, and the seeds of tall morningglory, cocklebur, velvetleaf, sicklepod, black nightshade and Japanese millet as well as the seeds of wheat, sugarbeet, corn, cotton and soybean were sowed therein and cultivated for 18 days. A designed amount of the test compound formulated into an emulsifiable concentrate according to Formulation Example 2 was diluted with water containing a spreading agent, and the dilution was sprayed onto the foliage of the test plants by means of a small hand sprayer at a spray volume of 5 liters per are. At the time of the application, the growing stage of the test plants varied depending on their species, but they were generally at the 1 to 4 leaf stage and in a height of 2 to 12 cm. The test plants were further grown in a greenhouse for 20 days, and the herbicidal activity was examined. The results are shown in Table 8.

TEST EXAMPLE 8

Vats (33 cm × 23 cm × 11 cm) were filled with upland field soil, and the seeds of soybean, cotton, sugarbeet, corn and wheat as well as the seeds of tall morningglory, cocklebur, velvetleaf, sicklepod, redroot pigweed, Japanese millet and johnsongrass were sowed therein and cultivated for 18 days in a greenhouse. A designed amount of the test compound formulated into an emulsifiable concentrate according to Formulation Example 2 was diluted with water containing a spreading agent, and the dilution was sprayed onto the foliage of the test plants by means of a small hand sprayer at a spray volume of 5 liters per are. At the time of the application, the growing stage of the test plants varied depending on their species, but they were generally at the 1 to 4 leaf stage and in a height of 2 to 12 cm. The test plants were further grown in the greenhouse for 20 days, and the herbicidal activity was examined. The results are shown in Table 9.

TABLE 8

| Compound No. | Dosage (g/are) | Herbicidal activity | | | | | | | | | | |
|---|---|---|---|---|---|---|---|---|---|---|---|
| | | Tall morning-glory | Cock-lebur | Velvet-leaf | Sickle-pod | Black night-shade | Japanese millet | Wheat | Sugar-beet | Corn | Cotton | Soy-bean |
| 2 | 1.25 | 5 | 3 | 5 | 2 | 5 | 5 | 5 | 5 | 5 | 5 | 4 |
|  | 0.32 | 3 | — | 5 | — | 5 | 2 | 3 | 5 | 4 | 5 | 3 |
| 6 | 1.25 | 5 | 5 | 5 | 4 | 5 | 5 | — | 5 | — | 5 | 3 |
|  | 0.32 | 5 | 4 | 5 | — | 5 | 5 | 0 | 3 | 0 | 5 | 3 |
| 7 | 0.32 | 5 | 4 | 5 | 4 | 5 | 5 | 1 | 5 | 1 | 5 | 4 |
|  | 0.08 | 5 | — | 5 | — | 4 | 3 | 0 | — | 0 | 5 | 4 |
| 8 | 1.25 | 5 | 3 | 5 | 2 | 5 | 5 | 1 | 3 | 3 | 5 | 4 |
|  | 0.32 | 4 | 3 | 3 | 2 | 4 | 4 | 1 | 1 | 2 | 2 | 2 |
| 9 | 1.25 | 5 | 3 | 5 | 3 | 5 | 5 | 4 | 5 | 3 | 5 | 4 |
|  | 0.32 | 4 | 1 | 5 | 0 | 5 | 2 | 1 | 1 | 0 | 5 | 3 |
| 15 | 0.32 | 5 | 5 | 5 | 4 | — | — | 2 | — | 1 | — | — |
|  | 0.08 | 4 | 4 | 5 | — | — | — | 0 | 0 | 0 | — | — |
| C | 5 | 5 | 5 | 5 | 3 | 5 | 2 | 3 | 5 | 3 | 5 | 5 |
|  | 1.25 | 3 | 3 | — | 1 | 3 | 1 | 3 | 4 | 2 | 5 | 5 |

TABLE 9

| Compound No. | Dosage (g/are) | Herbicidal activity | | | | | | | | | | |
|---|---|---|---|---|---|---|---|---|---|---|---|---|
| | | Soy-bean | Cotton | Sugar-beet | Corn | Wheat | Tall morning-glory | Cock-lebur | Velvet-leaf | Sickle-pod | Redroot pigweed | Japanese millet | Johnson-grass |
| 11 | 0.32 | 2 | 3 | — | 0 | 0 | 4 | 4 | 5 | — | 5 | 4 | 4 |
|  | 0.08 | 1 | 1 | — | 0 | 0 | 3 | 2 | 4 | — | 5 | 3 | 3 |
| 12 | 0.08 | 3 | 4 | 4 | 3 | 2 | 5 | 4 | 5 | — | 5 | 5 | 5 |
|  | 0.02 | 2 | 3 | 2 | 1 | 0 | 4 | — | 5 | — | 5 | 4 | 4 |
| 13 | 0.08 | 4 | 4 | 5 | 1 | 1 | 5 | 5 | 5 | 4 | 5 | 3 | 3 |
|  | 0.02 | 2 | 3 | 2 | 1 | 0 | 5 | 5 | 5 | — | 5 | 2 | 1 |
| 14 | 0.32 | 4 | 4 | 5 | 2 | 2 | 5 | 5 | 5 | 5 | 5 | 5 | 4 |
|  | 0.08 | 2 | 3 | — | 2 | 1 | 5 | 3 | 5 | 3 | 5 | 3 | 2 |

TABLE 9-continued

| Compound No. | Dosage (g/are) | Soybean | Cotton | Sugarbeet | Corn | Wheat | Tall morning-glory | Cocklebur | Velvetleaf | Sicklepod | Redroot pigweed | Japanese millet | Johnsongrass |
|---|---|---|---|---|---|---|---|---|---|---|---|---|---|
| D | 2.5 | 2 | 3 | 5 | 4 | 3 | 5 | 4 | 2 | 0 | 5 | 3 | 2 |
|  | 0.64 | 1 | 2 | 4 | 2 | 2 | 3 | 1 | 0 | 0 | 4 | 0 | 0 |

TEST EXAMPLE 9

Cylindrical plastic pots (diameter, 8 cm; height, 12 cm) were filled with paddy field soil, and the seeds of barnyardgrass, broad-leaved weeds (i.e. common falsepimpernel, toothcup, waterwort) and hardstem bulrush were sowed therein at a depth of 1 to 2 cm. After flooding the pots with water the buds of arrowhead were buried in 1 to 2 cm depth, and rice seedlings at the 2-leaf stage were transplanted therein. Cultivation was carried out in a greenhouse. Six days thereafter, a designed amount of the test compound formulated into an emulsifiable concentrate according to Formulation Example 2 was diluted with water (5 ml), and the dilution was applied to the pots by perfusion. The test plants were grown for further 20 days in the greenhouse, and the herbicidal activity was examined. The results are shown in Table 10.

TABLE 10

| Compound No. | Dosage (g/are) | Barnyardgrass | Hardstem bulrush | Arrowhead | Broad-leaved weed | Rice plant |
|---|---|---|---|---|---|---|
| 1 | 10 | 5 | 5 | — | 5 | 1 |
| 2 | 10 | 5 | 5 | 5 | 5 | — |
|  | 2.5 | 5 | 2 | 5 | 5 | 0 |
| 3 | 10 | 5 | 4 | — | 5 | 1 |
|  | 2.5 | 4 | 3 | — | 5 | 0 |
| 4 | 10 | 5 | 5 | — | 5 | 1 |
|  | 2.5 | 4 | 4 | — | 5 | 0 |
| 5 | 0.63 | 5 | 5 | 5 | 5 | — |
|  | 0.16 | 4 | 4 | — | 5 | 1 |
| 6 | 0.63 | 5 | 4 | 5 | 5 | 0 |
|  | 0.16 | 5 | 4 | — | 5 | 0 |
| 7 | 0.63 | 5 | 4 | 5 | 5 | — |
| 8 | 10 | 5 | 4 | 5 | 5 | — |
|  | 2.5 | 4 | — | — | 5 | 0 |
| 9 | 0.63 | 5 | 5 | — | 5 | 1 |
|  | 0.16 | 4 | 4 | — | 5 | 0 |
| 10 | 10 | 5 | 5 | — | 5 | 0 |
| A | 10 | 4 | 5 | 4 | 5 | 2 |
|  | 2.5 | 2 | 2 | 2 | 2 | 0 |
| B | 10 | 4 | 5 | 3 | 5 | 3 |
|  | 2.5 | 0 | 2 | 2 | 3 | 2 |
| C | 10 | 4 | 5 | 3 | 5 | 2 |
|  | 2.5 | 3 | 3 | 1 | 4 | 0 |

TEST EXAMPLE 10

Wagner's pots (1/5000 are) were filled with paddy field soil, and the seeds of barnyardgrass, broad-leaved weeds (i.e. common falsepimpernel, toothcup, waterwort) and hardstem bulrush were sowed therein and also the buds of arrowhead tided over the winter were buried in 1 to 2 cm depth. Water was poured therein to make a flooded condition. Rice seedlings at the 3-leaf stage were transplanted to the pots. Cultivation was carried out in a greenhouse. After three days. a designed amount of the test compound formulated into an emulsifiable concentrate according to Formulation Example 2 was diluted with water (10 ml), and the dilution was applied to the pots by perfusion, followed by addition of water thereto to make a 4 cm depth. The test plants were grown for further 20 days in the greenhouse, and the herbicidal activity was examined. For two days from the application, water was leaked with a 3 cm depth per day. The results are shown in Table 11.

TABLE 11

| Compound No. | Dosage (g/are) | Rice plant | Barnyardgrass | Broad-leaved weed | Hardstem bulrush | Arrowhead |
|---|---|---|---|---|---|---|
| 11 | 0.4 | 1 | 5 | 5 | 4 | 4 |
|  | 0.1 | 0 | 5 | 5 | 3 | 2 |
| 12 | 0.04 | 0 | 5 | 5 | 4 | — |
|  | 0.01 | 0 | 5 | 5 | 4 | — |
| 13 | 0.04 | 0 | 5 | 5 | 4 | 2 |
|  | 0.01 | 0 | 4 | 5 | 3 | — |
| 14 | 0.16 | — | 5 | 5 | 5 | 4 |
|  | 0.04 | 0 | 4 | 5 | 5 | 3 |
| 15 | 1.25 | 0 | 5 | 5 | 5 | 5 |
|  | 0.32 | 0 | 5 | 5 | 5 | 5 |
|  | 0.08 | 0 | 5 | 5 | 5 | 4 |
| 16 | 1.25 | 0 | 5 | 5 | 5 | 4 |
|  | 0.32 | 0 | 5 | 5 | 5 | 4 |
|  | 0.08 | 0 | 5 | 5 | — | — |
| B | 5 | 0 | 2 | 4 | — | 2 |
|  | 2.5 | 0 | 0 | 1 | — | 1 |

What is claimed is:

1. A compound of the formula:

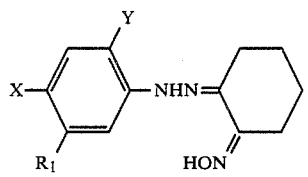

wherein $R_1$ is a hydrogen atom, a $C_1$–$C_4$ alkoxy group or a $C_1$–$C_4$ alkylthio group, X is a chlorine atom or a bromine atom and Y is a hydrogen atom, a fluorine atom or a chlorine atom.

* * * * *